(12) United States Patent
Pozzato

(10) Patent No.: US 7,713,267 B2
(45) Date of Patent: *May 11, 2010

(54) ELECTRONIC COAGULATION SCALPEL

(75) Inventor: Gianantonio Pozzato, Vicenza (IT)

(73) Assignee: Telea Electronic Engineering S.r.l., Sandrigo (VI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/525,046

(22) PCT Filed: Jun. 3, 2004

(86) PCT No.: PCT/EP2004/051021

§ 371 (c)(1),
(2), (4) Date: Feb. 18, 2005

(87) PCT Pub. No.: WO2004/107994

PCT Pub. Date: Dec. 16, 2004

(65) Prior Publication Data

US 2006/0167446 A1 Jul. 27, 2006

(30) Foreign Application Priority Data

Jun. 6, 2003 (IT) .......................... VI2003A0111

(51) Int. Cl.
*A61B 18/12* (2006.01)
(52) U.S. Cl. ......................................... 606/40; 606/39
(58) Field of Classification Search .................... 606/32, 606/33, 34, 39–42, 45, 46, 47–50
See application file for complete search history.

(56) References Cited

U.S. PATENT DOCUMENTS

| 4,517,976 | A | | 5/1985 | Murakoshi et al. |
| 4,534,347 | A | | 8/1985 | Taylor |
| 4,818,954 | A | * | 4/1989 | Flachenecker et al. ...... 331/183 |
| 4,860,745 | A | * | 8/1989 | Farin et al. .................... 606/40 |
| 5,011,483 | A | | 4/1991 | Sleister |
| 6,306,134 | B1 | | 10/2001 | Goble et al. |
| 6,458,122 | B1 | * | 10/2002 | Pozzato ....................... 606/37 |
| 6,835,195 | B2 | * | 12/2004 | Schulze et al. ................ 606/50 |
| 7,300,437 | B2 | * | 11/2007 | Pozzato ....................... 606/39 |

FOREIGN PATENT DOCUMENTS

WO         02053049 A1    7/2002

* cited by examiner

*Primary Examiner*—Lee S Cohen
(74) *Attorney, Agent, or Firm*—IP Strategies

(57) ABSTRACT

The invention relates to a method of regulating the power available at the manipulator of an electronic scalpel so as to make said manipulator adapted to be used to obtain blood clotting, said electronic scalpel being of the kind comprising: at least a mains voltage rectifying circuit supplying rectified and direct voltage to at least a radio frequency circuit adapted to emit as output a current carrier signal at a main frequency set by an oscillator, said current signal feeding said manipulator through a radio frequency transformer, wherein said method consists in applying to the manipulator a wave form resulting from the sum of the carrier wave and a modulating wave of such frequency that the energy transmitted to the tissue to be coagulated is such to raise the temperature of the tissue to be coagulated until denaturation of the fibrinogen contained therein is caused and transforming it into fibrin. The invention relates also to the electronic scalpel carrying out such a method

10 Claims, 2 Drawing Sheets

ELECTRONIC COAGULATION SCALPEL

BACKGROUND OF THE INVENTION

The present invention relates to an electronic scalpel for clotting blood vessels, adapted for surgical applications.

More particularly, as it will be better pointed out in the following description, the invention relates to an electronic scalpel adapted to transfer to the manipulator an electric power and therefore an energy adapted to carry out blood clotting in blood vessels without causing collapse of the vessel wall.

It is well known that blood clotting occurs because a proteinic substance dissolved in the plasma called fibrinogen during blood clotting is organized into a fibrous stable structure called fibrin.

In this way a fibrin mesh is obtained, preventing blood to come out from the blood vessel in which it flows.

Therefore enhancement of organization of fibrinogen into fibrin means to attain the conditions for blood clotting.

Tests have shown that coagulation, that is transformation of fibrinogen into fibrin occurs when to the plasma molecules such a kinetic energy is transferred as to increase their temperature at least up to 63° C. Under these conditions fibrinogen is transformed into fibrin without collapse of the blood vessel.

If a temperature of 80-85° C. is exceeded, the vessel collapses and the cells of the blood vessel wall die.

The presently available coagulation techniques carried out with electric scalpels cause a destruction of vessels creating a dead zone and moreover the electric scalpels operate with voltage values at dangerous levels sometimes of thousands of Volts.

The danger of high voltages together with the energy excess transmitted through the electric scalpels, causes destruction of the tissues of blood vessels as above mentioned.

Effected tests highlighted that the cells undergoing the action of the electronic scalpel, are not subject to necrotic degenerations when the energy transferred to break the molecular bond of these cells is substantially equal to the energy holding together said molecular bond.

As a matter of fact whenever energy is transferred to a cellular tissue, this causes the tissue molecules to vibrate and the increase of kinetic energy is transformed into a temperature increase of said tissue.

When temperature of the cells goes over 50° C., the cells necrotize and die.

Therefore it is extremely important to operate in such a way that the electronic scalpel carries out the cutting operation without producing heat in the surrounding tissue.

Moreover it was observed that the phenomenon of temperature increase does not occur when and only when the energy transferred to the tissue molecules is equal to the molecule bonding energy.

Indeed in this case the delivered energy is not used to increase the molecule kinetic energy, but only to break the bond joining the molecules to each other.

SUMMARY OF THE INVENTION

The object of the invention is to propose a method of regulating an electronic device transmitting the wave form to the manipulator of an electronic scalpel, as well as to carry out said electronic scalpel in such a way to transfer to the tissue area to be coagulated an energy substantially equal to the energy required to obtain a proteinic denaturation transforming the fibrinogen contained in plasma into fibrin without collapse of the blood vessel.

Another object is to obtain that the power transferred by the electronic scalpel is such as not to raise the temperature of the surrounding tissues to such high values as to cause collapse of the tissue of the blood vessel.

In other words an object is to obtain that the temperature transmitted by the manipulator of the electronic scalpel to the tissue to be coagulated never exceeds 70-75° C.

Another object of the invention indeed is to limit as much as possible or even totally prevent collapse of the blood vessels and therefore their destruction because the area no longer supplied with blood naturally dies.

A further objects is to provide an electronic scalpel using relatively low voltages for the coagulation so that the sometimes occurred possibility of intestine perforation is removed even when operating far from it.

The above mentioned objects and others that will be better highlighted in the following are attained by the electronic scalpel of the invention that according to the contents of the main claim is of the kind comprising:
- a manipulator for coagulation of organic tissues and at least an electrode to close the electric circuit being part of said manipulator;
- a rectifying circuit fed by the mains voltage supplying a rectified, direct or also stabilized voltage to a radio frequency circuit;
- a radio frequency circuit comprising at least an electronic switch fed by said rectified voltage and controlled by a pilot circuit emitting a generally square current wave of predetermined amplitude and frequency, wherein said electronic scalpel is characterized in that said radio frequency circuit has an output of a wave resulting from the combination of a generally square pulsating carrier wave and a modulating wave, said resulting wave circulating in a wide band resonant circuit at the frequency of said carrier wave.

Advantageously according to the invention at the manipulator one obtains at generally regular intervals, packets of waves that are resulting from the combination of a carrier wave with frequency equal to the resonant frequency of the circuit and a set of harmonics and a modulating wave with suitable frequency.

Each packet of waves available in the manipulator has an amplitude warranting a power and therefore an energy which is transferred to the cells involved in the coagulation and causing therein a light heating because the energy transmitted to said cells is different from the bonding energy of the molecules of said cells. In this way a heating is obtained that can be in the range of 65-70-75° C. but not higher than that, so as to obtain the effect of denaturation of the fibrinogen into fibrin but not necrosis of the surrounding cells.

Also advantageously the resonance frequency of the carrier wave is preferably but not necessarily chosen around 4 MHz while the modulating wave may have the mains frequency, for instance 50 or 60 Hz or a frequency of 20-30 KHz.

The presence of a spectrum of harmonics in the resulting wave causes the manipulator to transmit a power and therefore an energy to the tissue under coagulation, which is the sum of the different specific energies due to the various frequencies.

This is particularly important because at each molecule of the cellular tissue to be coagulated of different nature corresponds an ideal energy to be transmitted to reach in the present case, the correct temperature allowing transformation of the fibrinogen into fibrin without causing damages to the other adjacent cells.

According to an embodiment of the invention, the resulting modulated wave is obtained by enabling and disabling at intermittent intervals a BUFFER circuit allowing or preventing the crystal oscillator or an eventual frequency synthesizer to transmit its pulsation to the pilot circuit of the electronic switch.

Therefore in this case intermittent pulse trains are obtained, said pulse trains depending upon the frequency by which the microprocessor controlling the BUFFER circuit carries out its enabling and disabling activity.

In another embodiment of the invention the resulting wave is obtained by summing the carrier wave generated at the frequency of the crystal oscillator or an eventual frequency synthesizer and supplied by the pilot circuit to the base of the electronic switch, through a partially rectified mains wave which is connected to the collector of the electronic switch.

The so called basic modulation, namely effected generating pulse trains on the pilot circuit, is particularly used for high power machines while the modulation to the collector is used for low power machines.

BRIEF DESCRIPTION OF THE DRAWINGS

Further characteristics and features of the invention will be better highlighted in the following description of a particular embodiment of the invention given as an illustrative but not limiting example and shown in the accompanying sheets of drawings in which.

DESCRIPTION OF THE INVENTION

According to an executive embodiment of the invention, instead of the transformer 11 and the rectifying circuit with filter 20 a stabilized switching AC/DC converter can be used, or a transformer coupled with a rectifying circuit with filter having a stabilized switching DC/DC converter in output.

In any case, the voltage 201 outgoing from these rectifying circuits should be direct and stabilized, with a prefixed value preferably comprised for instance between 50 V and 200 V, where the chosen voltage value depends on the utilization of the operating equipment.

Alternatively, for the same intended use of the equipment, the voltage can be different for different functions.

For instance, the feeding voltage can come from two feeders with two different voltage values depending on the bipolar function and the single-polar function of said scalpel, present on the same equipment.

Figure 1:
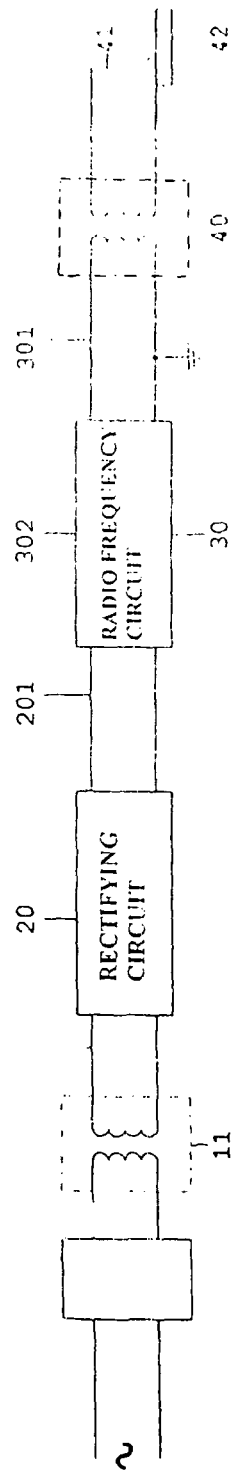
FIG. 1 is block diagram of the electronic scalpel of the invention.
Figure 2:
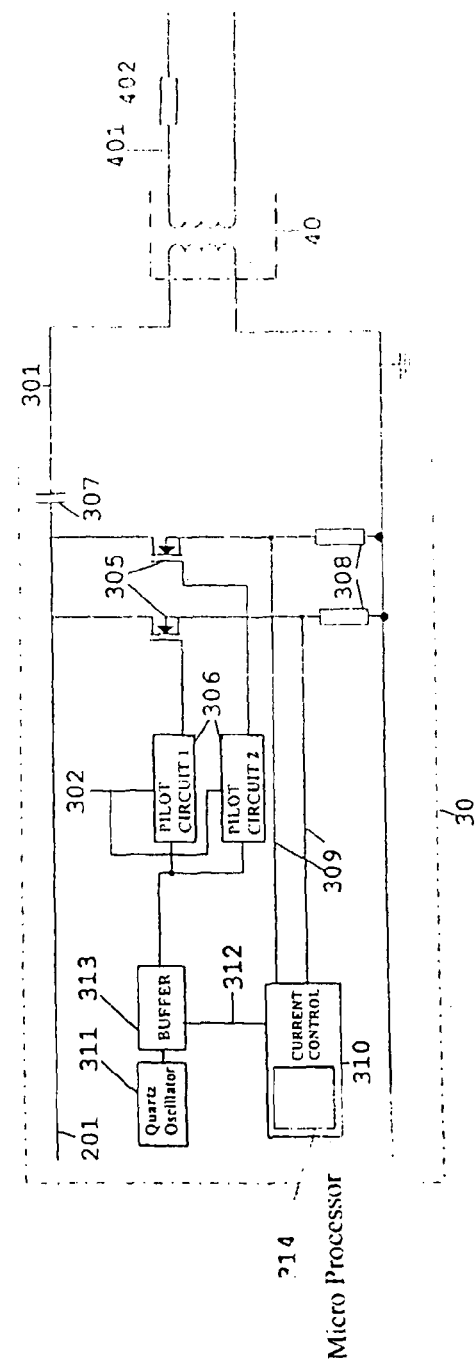
FIG. 2 is a detailed illustration of the radio frequency circuit of the electronic scalpel of FIG. 1.

This radio frequency circuit is better shown in FIG. 2.

The circuit in this example uses two electronic switches, for instance two MOSFET.

However, if an electronic scalpel requires higher cutting powers, it is possible to use three or more MOSFET components.

Each MOSFET 305 is controlled by a pilot circuit 306 fed by the voltage 302 supplied by a direct voltage stabilized power supply of known type, not shown in the drawings, in which it is possible to regulate the output voltage, which can be also of switching type, to obtain a better efficiency.

The pilot circuit 306 is also regulated by a current control 310 comprising among others a microprocessor 314 which interrupts, at prefixed intervals, the feeding of the pilot circuit so that the resultant wave which goes through the resonant circuit takes the form of a intermittent pulses train, each of them consisting of an amplitude modulated wave.

More particularly the radiofrequency circuit 30 provides that each MOSFET 305 acts as a switch breaking the direct current coming from the output voltage 201 of the rectifying circuit 20 and applied to the collector of each MOSFET.

Each pilot circuit 306 emits a unidirectional pulsating not alternated square wave 304 that drives the base of each MOSFET.

The frequency of the pilot circuit 306 is kept constant through a quartz oscillator 311 having an oscillation frequency of 4 MHz connected to a BUFFER 313.

The basic oscillation frequency of 4 MHz, and the higher frequencies too, can be also obtained by a circuit or a specific electronic device, like for instance a frequency synthesizer.

The control of MOSFET 305 occurs through a signal having an oscillation frequency equal to that of the quartz, or of the proper circuit or device, that in case of this example is 4 MHz.

The MOSFET 305 when closed interrupts the current on the leg 301 and when is open it lets the current to pass to the leg 301.

The width of the current wave form at 301 depends on the regulation of the signal 302 connected to the pilot circuit 306.

The regulation of the signal at 302, performed by a potentiometer not shown, or for example by a regulator of touch screen type, allows to choose the width of the output wave so as to obtain the power intended for the manipulator 41 of the electronic scalpel according to the operation to be carried out.

The following table shows the maximum powers employed in some application fields, using the scalpel of the invention in cutting operations according to the surgical intervention fields.

TABLE 1

| FIELD | POWER OF SCALPEL |
| --- | --- |
| Plastic Surgery | Max 90-100 W |
| Maxillo Facial | Max 90-100 W |
| Dermatology | 50-100 W |
| ENT | Max 100 W |
| Gynaecology | Max 100 W |
| Neurosurgery | Max 25 W |
| Urology | Max 120 W |

From table 1 one can see that the maximum power employed can range from a value lower than 25 Watts, for small dermatologic interventions, up to a maximum of 120 Watts.

To obtain a power adjustment method which is different from the one described in the example, providing for the power adjustment by the variation of the feeding voltage 302 of the drivers piloting the power MOSFETs gates, a still direct and stabilized (by AC/DC converter or by DC/DC converter), but variable for instance from 0 V to 200 V, voltage 201 can be used, while the voltage 302 is maintained steady.

Another possibility is that of using the direct and stabilized voltage 201, variable for instance from 0 V to 200 V, and the variable voltage 302 too to obtain in this case a power adjustment of mixed type.

According to a possible embodiment of the invention the basic oscillation frequency of 4 MHz is modulated through the intervention of the microprocessor 314 being part of the current control 310 arranging to transfer to the BUFFER circuit an enabling or disabling signal of said circuit with a frequency of 20-30 KHz and with a duty cycle less than 30%.

In this way the BUFFER circuit 310 transmits and breaks the oscillation generated by the oscillator 313 thus generating a pulse train reaching through the pilot circuit 306, the base of the electronic switch MOSFET 305.

The resulting wave 301 coming out from the MOSFET switches 305 is therefore a modulated wave whose amplitude is regulated by the power regulator 303.

According to another embodiment of the invention, a modulated resulting wave may be obtained instead of acting on the interruption of the crystal oscillator 311, by feeding the electronic switches MOSFET 305 with a voltage 201 which is no longer direct but is a partially rectified pulsating voltage (with single half wave).

In order to obtain this it is sufficient to modify the rectifying circuit 20 so that the signal 201 comes out from said circuit without the negative half wave and carries only the positive portion of the mains sinusoidal wave.

Also in this case one obtains an output current 301 from the radio frequency circuit having a resulting wave consisting of a carrier wave at 4 MHz and a modulating wave at 50-60 KHz.

As the output of the radio frequency circuit 30 is connected to the primary of the radio frequency transformer 40, a circulating current 301 is established passing through a resonant circuit at the frequency of 4 MHz, where the capacity and inductance of the resonant circuit are given by the eddy capacity of the MOSFET 305, the capacitor 307 of negligible reactance but acting as lock of the direct component of a voltage 201 and the inductance of the primary circuit of the transformer 40, respectively.

According to the invention, the resonant circuit on the carrier frequency is of the wide pass-band type so as to let pass even if dampened, at least the second and the third harmonic of the carrier wave relative to the signal 301.

Preferably it is desired that the signal 301 has at least the second, the third and the fourth harmonic.

To obtain a wide pass-band resonant circuit in the embodiment of FIG. 2 a high frequency transformer was used, having a number of turns of the secondary circuit greater than the number of turns of the primary circuit.

This because as it is known, the resonance coefficient Q is given by the formula:

$$Q = \omega\, C_R R_E = 2\Pi f\, C_R R_E =$$

where f is the resonance frequency, $C_R$ is the capacity of the resonant circuit, $R_E$ is the equivalent Resistance of the primary circuit when to the secondary circuit a load is applied consisting for instance of the patient's body to be operated with the electronic scalpel.

As the equivalent Resistance may be expressed by the formula:

$$R_E = R_C(\overline{N_2})$$

where $R_C$ is the load resistance and $N_1$ and $N_2$ is the number of turns of the primary and secondary respectively, one can see that the resonance factor Q may be expressed by the formula:

$$Q = 2\Pi f\, C_R R_C(\overline{N_2})$$

The formula points out that the resonance coefficient decreases when the number of the secondary turns increases relative to that of the primary turns.

The resonance coefficient may also be expressed with the formula $$Q = \frac{F_R}{B}$$

Where $F_R$ is the resonance frequency and B is the pass-band.

In the case of the invention, when it is desired to widen the pass-band of 4 MHz to 8 MHz, 12 MHz and 16 MHz, in the resonant circuit a transformer is inserted with a suitable number of turns so that the resonance coefficient be lower than 1, preferably between 0,4 and 0,6.

The modulating wave also circulating on the resonant circuit at the frequency of the carrier wave, generates several waves with a frequency out of resonance.

For this reason the resulting wave is rich of waves out of resonant frequency causing the effect to increase the temperature of the blood tissue to be coagulated.

These waves out of resonance frequency may be transferred to the manipulator because the resonance coefficient of the resonant circuit is sufficiently low.

Figure 3:
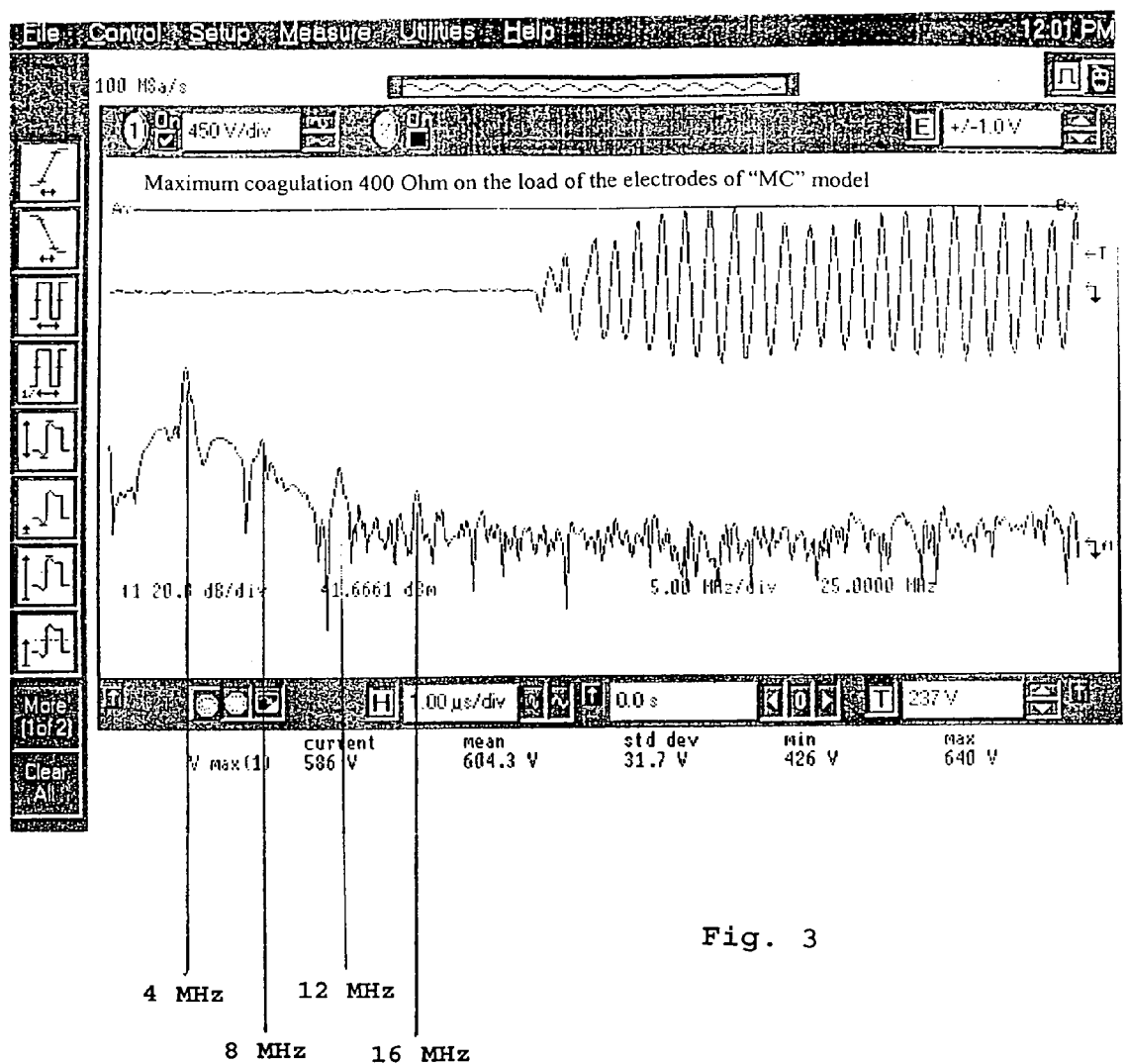
FIG. 3 shows the wave form of the power available at the manipulator of the electronic scalpel referred to the various frequencies.

With these characteristics of wide pass-band of the resonant circuit, the secondary current signal of the transformer at 401 takes the form shown in FIG. 3.

Checking the wave form of FIG. 3, one can see that at 4, 8, 12 and 16 MHz there are power peaks that are the interesting ones and are transferred to the scalpel manipulator with the above mentioned effects.

More particularly it was observed that the clotting obtained in the blood tissues is immediate and efficient.

The surrounding tissue does not undergo necrosis because the increase of temperature to 70-75° C. is limited to the specific clotting area and does not involve the area of the surrounding tissue.

The transformation of fibrinogen into fibrin is almost immediate.

One can see that the current of signal 401 once the power regulator 302 is set, is controlled through a current control coming from a current sensor 308 arranged after the MOSFET 305.

The voltage signal 309 coming from the current sensor 308 drives the current control 310 providing to limit through quick comparators controlled by the microprocessor 314, or by the microprocessor itself, the maximum current 401 acting with the signal 312 on the pilot circuit of the MOSFET.

In case of low impedance, as the current would rise to very high values, in the circuit there is a current limiter consisting of the inductance 402 limiting the current to the manipulator and hindering the circuit to exceed the maximum admissible current value.

The electric circuit is closed through the patient's ohmic load between two electrodes which are the manipulator 41 and a plate electrode 42.

The plate 42 is preferably covered by a light insulating layer to avoid plate burns to the patient, which are typical of the electronic scalpel.

One can see that the electrode assembly constituted by manipulator 41 and plate 42 may also take the different form of pincers with bipolar operation.

With the power adjustment method for the clotting electronic scalpel of the invention, it is possible to have an energy available at the manipulator which is substantially equal to the necessary one for having, in the cells interested by the clotting action, a rise in temperature barely sufficient to cause the fibrinogen denaturation, but lower than the temperature which would cause the death of the surrounding tissue cells.

As one can see, said energy dosage is obtained varying the amplitude of the power signal applied to the pilot circuit or to the feeding 201.

The consequence of said kind of manipulator energy dosage is to reduce at the least the post-operating stage pains, to considerably reduce the stay time of the patient in hospital after surgery and to consequently reduce hospitalization costs.

The clotting scalpel of the invention can be used as well without any problem for interventions on patients with pace-maker, because the frequencies used by the scalpel of the invention do not interfere with the correct pace-maker working.

The invention claimed is:

1. An electronic scalpel comprising:
   a manipulator having an electrode for cutting tissue and coagulation of blood;
   a rectifying circuit for supplying a rectified voltage and a direct voltage;
   a pilot circuit;
   a radio frequency circuit including an electronic switch fed by said rectified voltage and controlled by the pilot circuit for producing an output wave, said radio frequency circuit producing a resulting wave formed by the combination of a generally square carrier wave of a selected frequency and a modulating wave;
   a wide band resonant circuit for circulating the resulting wave at the frequency of said carrier wave, the pilot circuit produces an output for controlling the electronic switch to regulate the amplitude of the resulting wave to avoid destruction of the tissue;
   a regulator for modifying the rectified voltage of the pilot circuit wherein the resulting wave has an amplitude at the manipulator varied by means of said regulator such that the temperature of the tissue in which the coagulation takes place is in a range between about 50° C. and about 75° C., such temperature range resulting in denaturation of fibrinogen and its transformation into fibrin.

2. The electronic scalpel according to claim 1, wherein the switch has a parasitic capacity and a transformer feeding the manipulator, said transformer having a primary circuit with an inductance, said resonant circuit includes the parasitic capacity of said electronic switch and the inductance of the primary circuit of the transformer feeding said manipulator.

3. The electronic scalpel according to claim 1, wherein the amplitude of the resulting wave at the manipulator is variable by modification of the rectified and direct voltage which feeds said radiofrequency circuit.

4. The electronic scalpel according to claim 1, wherein the amplitude of the resulting wave at the manipulator is variable by modification of the rectified and direct voltage which feeds said radiofrequency circuit and by a regulator which modifies the voltage of the pilot circuit.

5. The electronic scalpel according to claim 1, wherein said pilot circuit is connected to a control circuit comprising a microprocessor interrupting at predetermined intervals an input to said pilot circuit so that the wave passing through the resonant circuit takes the form of a train of intermittent pulses, each comprising an amplitude modulated wave.

6. The electronic scalpel according to claim 1, wherein said switch has a collector and a modulating wave is applied to the collector of said electronic switch, said modulating wave comprising positive half cycles of the rectified voltage.

7. The electronic scalpel according to claim 1, wherein the carrier wave has a frequency of about 4 MHz.

8. The electronic scalpel according to claim 7, wherein the pilot circuit produces a pulse train having a frequency of about 20-30 KHz.

9. The electronic scalpel according to claim 7, wherein the modulating wave has a frequency of about 50 Hz.

10. The electronic scalpel according to claim 7, wherein the modulating wave has a frequency of about 60 Hz.

* * * * *